United States Patent
Panin et al.

(10) Patent No.: US 9,155,514 B2
(45) Date of Patent: Oct. 13, 2015

(54) RECONSTRUCTION WITH PARTIALLY KNOWN ATTENUATION INFORMATION IN TIME OF FLIGHT POSITRON EMISSION TOMOGRAPHY

(71) Applicant: Siemens Medical Solutions USA, Inc., Malvern, PA (US)

(72) Inventors: Vladimir Y Panin, Knoxville, TN (US); Michel Defrise, Brussels (BE); Johan Nuyts, Heverlee (BE)

(73) Assignees: Siemens Medical Solutions USA, Inc., Malvern, PA (US); Katholieke Universiteit Leuven, Leuven Research & Development, Leuven (BE); Vrije Universiteit Brussel, Brussels (BE)

( * ) Notice: Subject to any disclaimer, the term of this patent is extended or adjusted under 35 U.S.C. 154(b) by 0 days.

(21) Appl. No.: 14/444,210

(22) Filed: Jul. 28, 2014

(65) Prior Publication Data

US 2015/0036789 A1 Feb. 5, 2015

Related U.S. Application Data

(60) Provisional application No. 61/860,950, filed on Aug. 1, 2013.

(51) Int. Cl.
*A61B 6/00* (2006.01)
*G06T 11/00* (2006.01)
*A61B 6/03* (2006.01)

(52) U.S. Cl.
CPC .............. *A61B 6/5235* (2013.01); *A61B 6/032* (2013.01); *A61B 6/037* (2013.01); *A61B 6/4417* (2013.01); *A61B 6/5205* (2013.01); *G06T 11/006* (2013.01); *G06T 2207/10084* (2013.01); *G06T 2211/40* (2013.01)

(58) Field of Classification Search
CPC .... A61B 6/037; A61B 6/5235; G01T 1/2985; G06T 11/006
USPC ..................................... 250/363.04
See application file for complete search history.

(56) References Cited

U.S. PATENT DOCUMENTS

| | | | |
|---|---|---|---|
| 6,490,476 B1* | 12/2002 | Townsend et al. ............ 600/427 |
| 2007/0167716 A1* | 7/2007 | Kinahan et al. ............... 600/407 |
| 2008/0219525 A1* | 9/2008 | Panin et al. ................... 382/128 |

(Continued)

OTHER PUBLICATIONS

Y. Censor, et al., "New approach to the emission computerized tomography problem: simultaneous calculation of attenuation and activity coefficients," IEEE Trans. Nucl. Sci., vol. 26, pp. 2775-2779, 1979.

(Continued)

*Primary Examiner* — Marcus Taningco
(74) *Attorney, Agent, or Firm* — Peter Kendall

(57) ABSTRACT

Reconstruction in positron emission tomography is performed with partially known attenuation. A PET-CT scanner is used to generate a PET image with time of flight emission information. To limit x-ray dose while providing increased sensitivity at the ends of the CT volume in the PET image, attenuation coefficients for oblique LORs passing outside the CT volume are determined from the time of flight emission information. The attenuation coefficients for LORs within the CT volume are derived from the CT data. An objective function may be maximized for the emission distribution without reconstructing the attenuation distribution.

20 Claims, 6 Drawing Sheets

(56) References Cited

U.S. PATENT DOCUMENTS

2013/0028496 A1* 1/2013 Panin et al. .................. 382/131
2015/0065854 A1* 3/2015 Ahn et al. .................... 600/411

OTHER PUBLICATIONS

A. Welch, et al., "Toward accurate attenuation correction in SPECT without transmission measurements," IEEE Trans. Med. Image, vol. 16, pp. 532-542, 1997.

J. Nuyts, et al., "Simultaneous maximum a posteriori reconstruction of attenuation and activity distributions from emission sonograms," IEEE Trans. Med. Image., vol. 18, pp. 393-403, 1999.

M.S. Kaplan, et al., "A Differential attenuation method for simultaneous estimation of SPECT activity and attenuation distributions," IEEE Trans. Nucl. Sci., vol. 46, pp. 535-541, 1999.

A.V. Bronnikov, et al., "Reconstruction of attenuation map using discrete consistency conditions," IEEE Trans. Med. Imag., vol. 19, pp. 451-462, 2000.

H. Kudo, et al., "A new approach to SPECT attenuation correction without transmission measurements," 2000 IEEE Nucl. Sci. Symp. Med. Imag. Conf., pp. 13/58-13/62, 2000.

A. Krol, et al., "An EM algorithm for estimating SPECT emission and transmission parameters from emission data only," IEEE Trans. Med. Imag., vol. 20, pp. 218-232, 2001.

M. Defrise, et al., "Time-of-flight PET data determine the attenuation sonogram up to a constant," Phys. Med. Bio., vol. 56, pp. 885-899, 2012.

A. Rezaei, et al., "Simultaneous Reconstruciton of Activity and Attenuation for Time-of-Flight PET," IEEE Trans. Med. Imag. Accepted, 2012.

A. Salomon, et al., "Simultaneous Reconstruction of Activity and Attenuation for PET/MR," IEEE Trans. Med. Imag., vol. 30m pp. 804-813, 2011.

V.Y. Panin, et al., "Simultaneous reconstruction of emission activity and attenuation coefficient distribution from TOF data, acquired with rotating external line source," 2011 IEEE Nucl. Sci. Symp. Med. Imag. Conf., M5-202, pp. 4329-4336, 2011.

J. L. Nuyts, et al., "ML-Reconstruction for TOF-PET with Simultaneous Estimation of the Attenuation Factors," 2011 IEEE Nucl. Sci, Symp. Med. Imag. Conf., M04-1, 2011.

A.R. De Pierro, "On the relation between the ISRA and the EM algorithm for positron emission tomography," IEEE Trans. Med. Imag., vol. 12, pp. 328-333, 1993.

* cited by examiner

RECONSTRUCTION WITH PARTIALLY KNOWN ATTENUATION INFORMATION IN TIME OF FLIGHT POSITRON EMISSION TOMOGRAPHY

RELATED APPLICATIONS

The present patent document claims the benefit of the filing date under 35 U.S.C. §119(e) of Provisional U.S. Patent Application Ser. No. 61/860,950, filed Aug. 1, 2013, which is hereby incorporated by reference.

BACKGROUND

The present embodiments relate to positron emission tomography (PET). In PET, attenuation information is used in reconstruction. The attenuation is derived from a computed tomography (CT) or other x-ray scan. There is a desire to limit the use of x-rays.

A three-dimensional PET scanner acquires oblique lines of response (LORs) in addition to the direct plane LORs. As a result, the edge axial planes of the reconstructed volume suffer from a lower sensitivity than the central axial planes because the edge axial planes are reconstructed from a smaller set of oblique LORs. A CT scan, which is acquired first, defines the axial extent of the reconstructed volume. Typically, the axial coverage length is chosen in such a way that a certain number of overlapping PET bed positions completely sample the reconstruction volume. The bed overlap is designed to achieve a uniform sensitivity by summing the roughly triangular axial sensitivity profiles corresponding to each bed position. Nevertheless, the edge planes of the last bed acquisition still have a lower sensitivity because only direct plane LORs are available. This problem can be solved by acquiring an additional bed position, so as to make the axial sensitivity more uniform throughout the CT defined volume. The problem is not yet solved however, because the attenuation correction factors (ACFs) for some oblique LORs are not available from the CT scan because these LORs are passing outside the CT defined volume. As a result, the edge axial planes would still suffer from a lower sensitivity if only LORs with CT-known ACFs are used during reconstruction. Increasing x-ray dose to increase the CT volume is not desired.

To avoid this issue, reconstruction may be performed without x-ray based attenuation information. In PET, simultaneous emission activity and attenuation map reconstruction in non-time of flight (TOF) PET has been a topic of investigation in order to exclude the x-ray transmission sources completely. Both distributions are assumed to be reconstructed from a single emission data set. A significant amount of information about attenuation is contained in the emission data. The artifact of cross-talking between the activity and the attenuation images, when the activity image features propagate to attenuation map images and vice versa, is difficult to avoid.

Recent theoretical investigations concluded that both activity and attenuation distributions may be determined from PET TOF data up to an activity image scaling parameter. These advances encouraged investigation of practical applications of transmission less TOF reconstruction. One limitation of this approach is that the attenuation information cannot be determined outside of the emission sinogram support. In addition, the solution may not be sufficiently stable. Therefore, the practical application might still require a priori knowledge of the attenuation. Recent examples of simultaneous activity and attenuation reconstruction in TOF PET indeed use a significant amount of prior information. MRI data may be used to define regions of uniform attenuation and estimate the attenuation coefficient in each region from the emission TOF data. Derived truncated attenuation map regions have been used in the application for PET-MRI. Another example is the use of additional external nuclear transmission sources. This approach is difficult when using emission data alone for general cases, such as when attenuation map support is larger compared to activity image support.

BRIEF SUMMARY

By way of introduction, the preferred embodiments described below include methods, systems, and non-transitory computer readable media for reconstructing in positron emission tomography with partially known attenuation. A PET-CT scanner is used to generate a PET image with time of flight emission information. To limit x-ray dose while providing increased sensitivity at the ends of the CT volume in the PET image, attenuation coefficients for oblique LORs passing outside the CT volume are determined from the time of flight emission information. The attenuation coefficients for LORs within the CT volume are derived from the CT data. An objective function may be maximized for the emission distribution without reconstructing the attenuation distribution.

In a first aspect, a method is provided for reconstructing in positron emission tomography with partially known attenuation. A computed tomography (CT) scanner acquires attenuation information for a CT volume of a patient. A positron emission tomography (PET) scanner having a plurality of detectors acquires time of flight data along lines-of-response from emissions. The attenuation information is converted into attenuation coefficients along only a first subset of a plurality of the lines of response where a second sub-set of the lines of response are missing attenuation information. An image of the patient is reconstructed from the time of flight data including the lines of response of the first and second subsets. The reconstruction is a function of the attenuation coefficients along the lines of response of the first subset and a model of attenuation coefficients along the lines of response of the second subset. The model is a function of the corresponding time of flight data for the lines of response of the second sub-set. The image is displayed.

In a second aspect, a non-transitory computer readable storage medium has stored therein data representing instructions executable by a programmed processor for reconstructing in positron emission tomography (PET) with partially known attenuation. The storage medium includes instructions for reconstructing a PET emission distribution from emission data for lines of response and from attenuation coefficients for some but not all of the lines of response, the reconstructing being free of reconstructing an attenuation distribution; and generating a PET image from the PET emission distribution.

In a third aspect, a system is provided for reconstructing in positron emission tomography (PET) with partially known attenuation. An x-ray scanner is configured to obtain attenuation data for a patient volume. A bed is configured to move to scan different parts of a patient in a positron emission tomography (PET) scan. Rings of detectors spaced axially are operable to perform the PET scan along lines of response between the detectors. A first set of lines of response oblique to the axial spacing of the detectors extend out of the patient volume. A processor connects to the detectors. The processor is configured to reconstruct activity distribution using time of flight for detected emissions along the lines of response including the first set and others. The activity distribution is reconstructed with attenuation corrections from the attenuation data for the others of the lines of response and from the time of flight for the detected emissions for the first set of lines of response.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A more uniform sensitivity emission image is reconstructed with partially known axial attenuation information in a PET-CT scanner. In PET-CT, the axial length of image reconstruction is defined by the CT scan, which delivers an axial extent-dependent radiation dose. The beginning and end scanning points for CT and therefore PET scans are typically chosen in such a way that the PET scan is performed with a particular number of beds or range of bed movement. Still, the edge planes will have lower sensitivity due to the absence of oblique LOR attenuation factors unless the CT volume and corresponding x-ray dose extends beyond the region of interest.

ACFs are used for sensitivity restoration of oblique LORs and are accumulated over the attenuation map image beyond CT scanning points. ACFs are partially known. An iterative algorithm to reconstruct only the emission image, with estimation of partially unknown ACFs, is presented. The missing oblique ACFs are estimated simultaneously with the emission image reconstruction, so as to restore uniform sensitivity of the whole targeted volume. The estimation of ACFs is a sub-product of emission activity reconstruction.

ACFs and emission activity may be defined only up to a scaling parameter. This is due to the fact that ACFs and emission activity projections are multiplied in the modeling of measured data. This scaling issue may be avoided by enforcing constraints on the attenuation coefficients in TX-less algorithms that reconstruct the attenuation map. Since the attenuation map is not reconstructed, but rather the ACFs are used directly, this approach of avoidance is not used. Instead, the scaling parameter is defined implicitly by the interconnection between the direct and oblique LORs, for which the ACFs are known from the CT, and those edge oblique LORs for which the ACFs is estimated from the emission data. Partial ACF knowledge restores attenuation information necessary for the uniform sensitivity of PET reconstructed volume edge planes.

The scatter distribution is available with the partial ACF since the scatter is calculated based on the direct planes, and then simply extrapolated to the oblique LORs. In addition, the scatter distribution is a smooth function, which may be extrapolated beyond the target volume.

The reconstruction is of a similar complexity to commonly used maximum likelihood-expectation maximization (ML-EM) or the ML(OS)-EM. A Poisson model reconstruction in the presence of background events is used, but other models of reconstruction are possible. The model is also applicable when no prior attenuation map is available, such as full unknown ACF.

Figure 1:
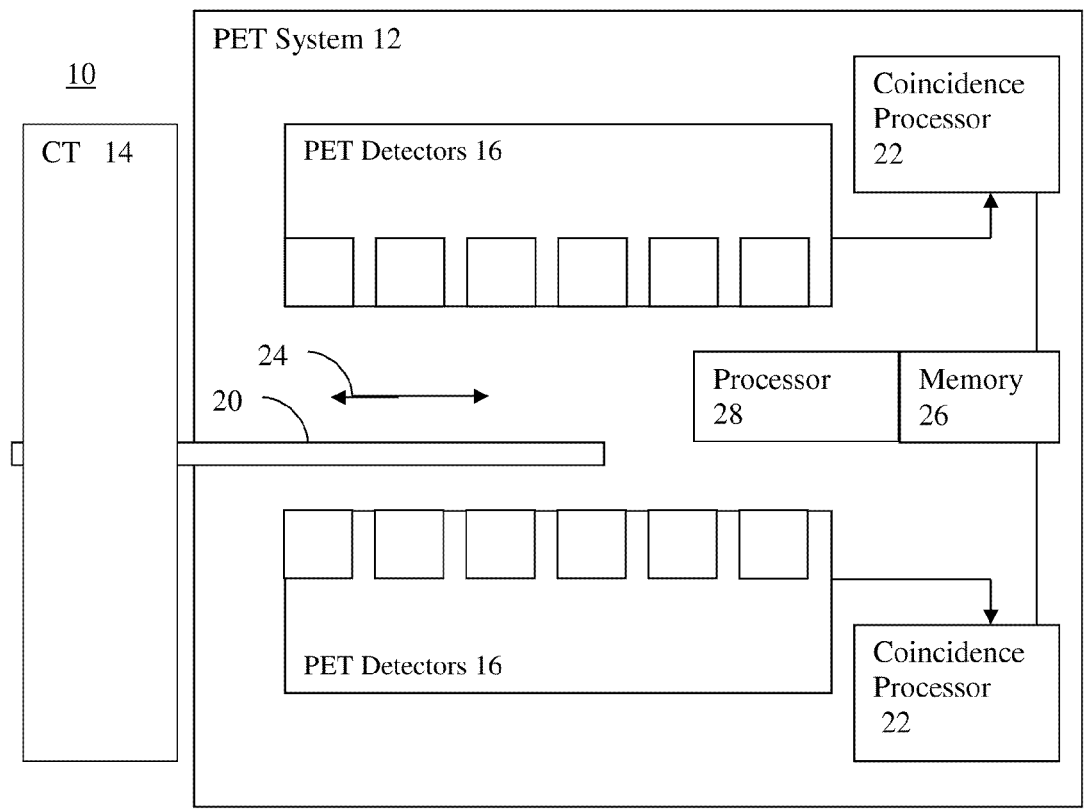
FIG. 1 is a block diagram of a system, according to one embodiment, for reconstructing in positron emission tomography with partially known attenuation.

FIG. 1 shows a PET-CT system 10 for reconstructing in positron emission tomography (PET) with partially known attenuation. The PET-CT system 10 includes a CT scanner 14 and PET system 12. The PET system 12 includes rings of detectors 16, a bed 20, coincidence processors 22, a memory 26, and a processor 28. The processor 28, memory 26, and/or a display are part of the PET system 12 or are separate (e.g., a computer or workstation). Additional, different, or fewer components may be provided. For example, the system is a computer without the detectors 16 and bed 20, instead relying on data acquired by a separate scanner. As another example, the PET-CT system 10 includes power supplies, communications systems, and user interface systems.

The CT system 14 includes an x-ray source and opposing detector mounted in a gantry. The CT system 14 is an x-ray scanner configured to obtain attenuation data for a patient volume. The gantry moves the source and detector about the patient for scanning. The processor 28 or a different processor computes the attenuation of the x-rays at different voxels within the scan volume. Any now known or later developed CT system may be used. Other x-ray scanners, such as a CT-like C-arm scanner, may be used.

The CT system 14 is within a same housing as the PET system 12 or is spaced apart by and connected by a common track for the bed 20. Completely separate CT system 14 and PET system 12 may be used.

The bed 20 is a gurney, table, or other support to hold an examination subject, such as a patient. A robot, gears, cable, track, and/or other device move the bed 20. The movement is along an axial dimension represented by double arrow 24. The detectors 16 and/or PET scanner 10 form a bore or hollow cylinder through which the bed 20 moves the patient. The distance from the axial axis is the radial distance. The angle about the axial axis is the azimuth. Other coordinate systems, such as a cylindrical or polar coordinate system, may be used.

In one embodiment, the movement is continuous, at least during part of the scanning. The bed 20, while supporting the patient, is moved at a same or a varying velocity along the axial dimension 24. For example, the head of the patient is scanned with 1.5 mm/s movement of the patient, and the torso is scanned with 1.0 mm/s movement of the patient. Other combinations of the same or different rates, with or without a greater number of different velocities, may be used. The movement may pass the patient through the bore or merely partly into the bore. The movement is with or without acceleration. In one embodiment, the movement is back and forth, scanning the patient multiple times in a cyclical pattern. A single pass may be used in other embodiments.

In other embodiments, the bed 20 is positioned to two or more discrete bed positions. PET scanning occurs over a period with the stationary bed at each bed position. The bed positions are spaced so that the PET scan volume (e.g., the volume within or between the detectors 16) overlaps in the adjacent bed positions. The bed 20 is moved from position to position in order to acquire PET data for the PET scan.

With either stationary bed positions or continuous bed motion, the bed 20 moves the patient to scan the CT volume for emissions. For more uniform sensitivity, the end extent of the bed positions extends the detectors 16 to collect emissions along oblique lines of response through the edge or end of the CT volume. CT information is not available along the entire length of the oblique lines of response extending past the CT volume.

The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

Figure 2:
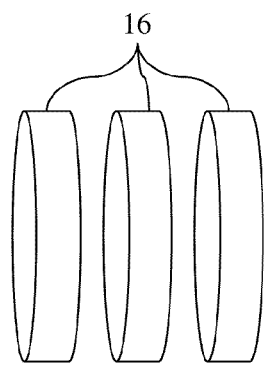
FIG. 2 shows example rings of detectors.

The detectors 16 are arranged individually or in groups. Blocks or groups of detectors 16 are arranged in any pattern around the bore. FIG. 2 represents blocks of detectors 16 arranged as separate rings around the bore. The rings are shown spaced apart, but are placed adjacent or abutting each other. Any gap may be provided between blocks within a ring, detectors within a block, and/or between rings. Any number of detectors in a block (e.g., 8 or 16), detector blocks in a ring, and/or rings may be used. The rings may extend completely or only partially around the bore.

The PET system 10 is a nuclear imaging system. The detectors 16 detect gamma rays emitted indirectly by a positron-emitting tracer. Pairs of gamma rays generated by a same positron may be detected using the ring of the detectors 16. The pairs of gamma rays travel about 180 degrees apart. If the direction of travel intersects the arrangement of detectors 16 at two locations, a coincident pair may be detected. To distinguish specific pairs, the coincidence of detected gamma rays is determined. The timing of receipt is used to pair the detected gamma rays. The timing, as prompt data, may also indicate the time of flight, providing information about where along a line of response the emission occurred.

As the bed 20 moves, the patient passes through the rings. A given part (e.g., organ) of the patient is within different rings at different times due to the continuous bed motion or bed position. The line-of-responses for the same part of the patient and corresponding actual three-dimensional location (i.e., point along the line-of-response) is at different locations at different times. The detectors 16 continue to detect gamma rays as the bed 20 and patient moves so different lines-of-response may be for the same part of the patient at different positions within the bore.

The lines of response include direct plane LORs corresponding to lines perpendicular to the axis of movement of the bed 20 or axial spacing of the detectors 16. The lines of response also include oblique LORs corresponding to lines that are at a non-perpendicular angle to the axis of movement of the bed 20 but still intersecting the detectors 16.

Each individual detection output from the detectors 16 includes energy, position, and timing information. Alternatively, the detectors 16 output energy information and a receiving processor determines the timing and position (e.g., based on port assignment or connections). The timing information is used to determine coincidence of detection by different detectors by the coincidence processors 22 as well as general position along the line of response of the emission. Pairs of gamma rays associated with a same positron emission are determined. Based on the detected event, a line-of-response is determined given the detectors involved in the detection of that event.

The detected events are passed to the memory 26 and/or processor 28. The processor 28 connects with the detectors 16, such as through the coincidence processors 22. The processor 28 also connects with the CT system 14 to receive attenuation information.

The processor 28 is a general processor, digital signal processor, graphics processing unit, application specific integrated circuit, field programmable gate array, digital circuit, analog circuit, combinations thereof, or other now known or later developed device for processing detected line-of-response events, modeling ACF, and/or reconstructing. The processor 28 is a single device, a plurality of devices, or a network. For more than one device, parallel or sequential division of processing may be used. Different devices making up the processor 20 may perform different functions, such as one processor for handling line of response emission information and attenuation information and another processor for reconstructing the object (i.e., patient) space. In one embodiment, the processor 28 is a control processor or other processor of the PET-CT system 10 or the PET system 12. In other embodiments, the processor 28 is part of a separate workstation or computer.

The processor 28 operates pursuant to stored instructions to perform various acts described herein. The processor 28 is configured by software and/or hardware to perform any or all of the acts of FIG. 3. The operation and configuration of the processor 28 is first described in general below. An example implementation, as well as theory behind the operation, is described in more detail in the following discussion of FIG. 3.

The processor 28 is configured to reconstruct the activity distribution using the time of flight (TOF) for detected emissions along the lines of response. The TOF from the direct plane and oblique lines are used to reconstruct the activity distribution. To account for differences in attenuation due to different tissues or obstructions along the different lines of response, the ACFs or integrated attenuations along the corresponding lines of response are used in the reconstruction. For some of the lines of response, attenuation information may not be available. Where part of the line of response through the patient includes voxels or regions for which attenuation information is not available, part of the contributing attenuation for the ACF is not provided. As a result, ACF is not known for that line of response.

The processor 28 is configured to reconstruct the activity distribution both with attenuation corrections from the attenuation data for some of the lines of response and with attenuation corrections estimated from the time of flight information for the detected emissions for lines of response missing attenuation information. In one embodiment, the reconstruction is of the activity distribution without also reconstructing a distribution of the attenuation. Instead, the known ACF and emission-based estimates of ACF for the lines of response are used in the object function.

The processor 28 uses the events (e.g., line-of-response events) and ACF stored in the memory 26 for processing. For processing, the data bypasses the memory 26, is temporarily stored in the memory 26, or is loaded from the memory 26.

The detected events, line-of-response information (e.g., sinograms), time step, prompt data, attenuation information, ACF, reconstructed image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 12 or a remote workstation or database, such as a PACS memory.

The memory 26 is additionally or alternatively a non-transitory computer readable storage medium with processing instructions. The memory 26 stores data representing instructions executable by the programmed processor 28 for reconstructing in positron emission tomography (PET) with partially known attenuation. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 12 may include a display. For example, the processor 28 reconstructs the patient or object being scanned from the line-of-response and attenuation data. The reconstruction is used for three-dimensional rendering, multi-planar reconstruction, or two-dimensional imaging of the function of the object or patient. The images are displayed on the display. The display is a CRT, LCD, plasma screen, projector, printer, or other output device for showing an image.

Figure 3:
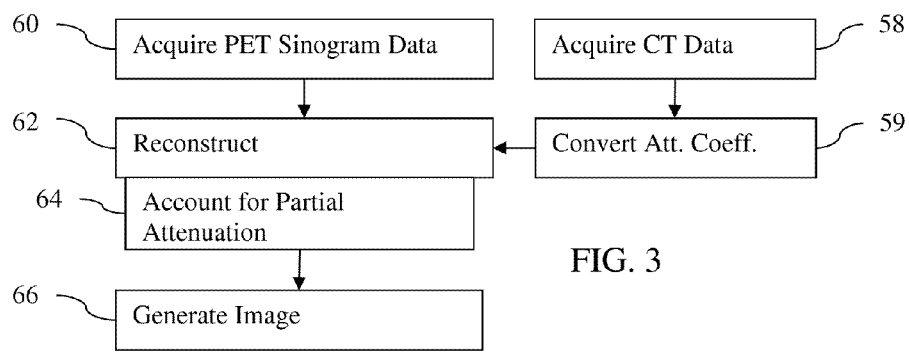
FIG. 3 is a flow chart of an embodiment of a method for reconstructing in positron emission tomography with partially known attenuation.

FIG. 3 shows a method for reconstructing in positron emission tomography with partially known attenuation. The method of FIG. 3 is implemented by the processor 28, the PET system 12, the PET-CT system 10, and/or other component or system. Additional, different, or fewer acts may be performed. For example, act 66 is not performed. The acts are performed in the order shown or a different order. Acts 58 and 59 may be performed prior to, at a same time as, or after act 60. As another example, act 59 may occur after act 60.

In act 58, attenuation information is acquired. A CT scan of the patient is performed by the CT scanner. Other x-ray scanners to measure the attenuation at different locations or along lines through the patient may be used. Alternatively, the attenuation information is acquired from memory, such as attenuation information from a previously performed CT scan.

The CT scan is of a volume of the patient. Any range of the patient may be scanned, such as from the hips to the neck. The entire patient may be scanned. The CT scan provides measures of attenuation of the x-ray energy at different locations, such as voxels, within the patient. The attenuation of the voxels is computed by tomography from a sequence of x-ray scans from different angles through the patient. The resulting CT intensity data represents voxels of the CT scan volume.

In act 60, PET sinogram data is acquired. Time of flight (TOF) data for emissions detected along a plurality of lines of response is acquired. The acquisition is by scanning with the PET scanner with a plurality of detectors. In alternative embodiments, the acquisition is by transfer or upload from a memory.

Figure 4:
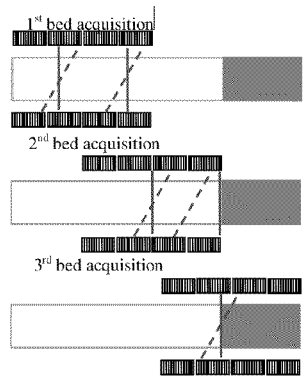
FIG. 4 illustrates example bed positions and lines of response.

Gamma rays are detected by one or more rings of detectors or other grouping of detectors. The patient ingests or is injected with a radiopharmaceutical. The radiopharmaceutical includes an isotope. The isotope decays over time, resulting in generation of a positron.

Where each ring is formed from a block of X detectors along the axial direction, X planes are defined. For example, each block includes 16 detectors, so 16 planes are provided for each block. Where there are 50 rings, 530 planes are defined. FIG. 4 shows lines of response for three different bed positions as solid vertical lines. These lines of response are direct plane lines. For each bed position, emissions along 530 or other number of direct plane lines of response may be detected.

Figure 6:
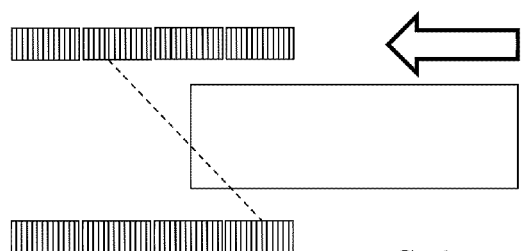
FIG. 6 illustrates an example continuous bed motion and line of response.

Since the detectors have an axial extent, emissions from lines of response oblique to the axis of the bed or detectors are detected. Example oblique lines of response are shown in FIGS. 4 and 6 as dashed lines.

In both continuous bed motion (FIG. 6) and use of discrete bed positions (FIG. 4), the same detectors are used to detect positron-electron annihilations from different parts of the patient. Due to the motion or change in position, annihilations in a same part of the patient may be detected at different rings at different times even where the line of gamma ray propagation is the same relative to the patient for each time. Of course, the line of propagation may be different at different times for a same location of the patient.

Line-of-response events from a patient are detected. The acquisition occurs over any period. For example, the acquisition is over 1, 10, 100, or other number of minutes. The PET scanning acquires detected emission events for functional information. The detected gamma rays are checked for coincidence to define lines-of-response, and the time difference or relative timing for coincident detections is recorded as prompt data. Any time window may be used for coincidence processing, such as 0.2 microsecond coincidence time window. Each detected emission event corresponds to a line or part of a line through a patient. By detecting emission events from different angles around a patient, a volume may be reconstructed.

In one embodiment, the time of flight data is obtained from different discrete, overlapping bed positions. Scanning is performed for each of any number of different overlapping bed positions. FIG. 4 shows an example with three different bed positions.

In another embodiment, the time of flight data is obtained while the bed is moving the patient. The movement is over any range of motion, such as for scanning all or only a part of the patient. The bed may move cyclically during the period, such as moving back and forth once, five times, ten times, twenty times, forty times, or other number of times. Alternatively, the bed moves in one direction only during the scan.

The motion of the bed is continuous over at least a portion of the acquisition period. Continuous is used in the sense of motion occurring during the scanning. The continuous motion may cease or have different velocities for a part of the scanning. With cyclical motion, there may be one or more times of no motion and parts of the period with acceleration or deceleration. In alternative embodiments, a constant velocity is provided.

Figure 5A:
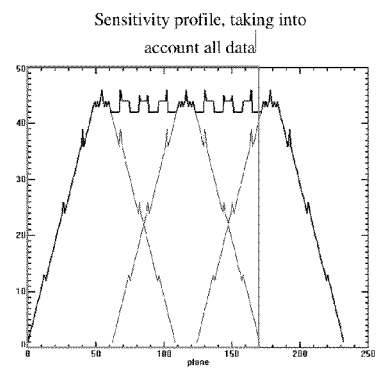
FIGS. 5A and 5B are example sensitivity profiles for the bed positions of FIG. 4.
Figure 5B:
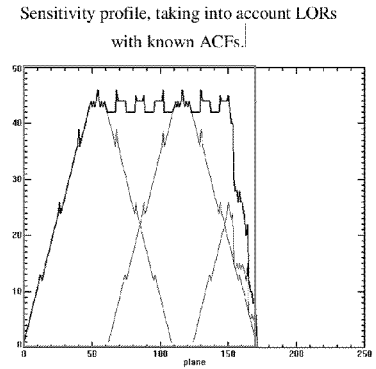
Figure 8:
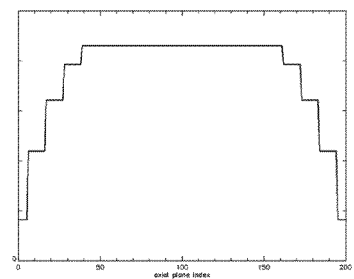
FIG. 8 is another example sensitivity profile for the bed motion of FIG. 6.

The acquisition is for any part of the patient. For the greatest axial position of the bed, the resulting reconstruction may have less sensitivity. The edge axial planes of the reconstructed volume suffer from a lower sensitivity than the central axial planes because the edges are reconstructed from a smaller set of oblique LORs. The CT scan defines the axial extent of the reconstructed volume (see white box of FIG. 4). Typically, the axial coverage length is chosen in such a way that a certain number of overlapping PET bed positions completely sample the reconstruction volume, as defined by the CT volume. The bed overlap is designed to achieve a uniform sensitivity by summing the roughly triangular axial sensitivity profiles corresponding to each bed position (see FIG. 5A). Nevertheless, the edge planes of the last bed acquisition still have a lower sensitivity because only direct plane LORs are available. This problem can be solved by acquiring an additional bed position (the third one shown in FIG. 4) or moving the bed over a greater range in continuous bed motion (see FIG. 6), so as to make the axial sensitivity uniform throughout the CT defined volume (see FIG. 8). As represented by the dashed lines in FIGS. 4 and 6, the attenuation correction factors (ACFs) for some oblique LORs are not available from the CT scan because these LORs are passing outside the CT defined volume (white box). As a result, the edge axial planes may still suffer from a lower sensitivity if only LORs with CT-known ACFs are used during reconstruction, as shown in FIG. 5B. The sensitivity profiles of FIGS. 5A, 5B, and 8 are obtained by Inverse Single Slice Rebinning (ISSRB) assuming axially uniform objects.

Referring again to FIG. 3, the attenuation information is converted into attenuation coefficients in act 59. The attenuation information is converted to account for differences in energy level between the x-rays and the photons of positron emission. For example, the attenuation information is converted into 511 coefficients.

The conversion also accounts for the lines of response. The measured attenuation information is for voxels in the CT volume. Any given line of response traverses the volume, so the attenuation along the line is an integral of the attenuations of the line. For the planar and oblique lines of response with known attenuation, at least through the patient, the attenuation information is converted into attenuation coefficient factors (ACFs). Known ACF is provided for only a subset of all of the lines of response. Some of the oblique lines of response have known attenuation through the patient.

Other oblique lines of response have at least a part of the line with unknown attenuation in the patient. The oblique lines of response passing outside of the CT volume while within the patient have missing attenuation information. The ACF for such a line is incomplete, so unknown. In the examples of FIGS. 4 and 6, the example oblique lines of response at the end bed positions that pass partly out of the CT volume have missing attenuation information. While some attenuation is known, the attenuation along the entire line within the patient is not known. Accordingly, the ACF is not known.

In act 62, an image of the patient is reconstructed from the time of flight data for the lines of response and the known ACFs. The object space is reconstructed form the PET TOF, such as from prompt data. The activity distribution in three-dimensions is reconstructed. The activity distribution is used for imaging, such as volume rendering, multi-planar reconstruction, or planar imaging.

Any reconstruction may be used. In one embodiment, the reconstruction is a Poisson iterative reconstruction, such as a maximum likelihood reconstruction. OSEM, FORE, or other reconstructions may be used. The reconstruction estimates the object or patient space from the lines-of-response. The detected events are used to iteratively determine the object space using forward, backward, or forward and backward projection.

The reconstruction accounts for the attenuation using ACFs for the lines of response. The lines of response used include lines of response for which ACF is known and lines of response for which ACF is not known. The PET emission distribution is reconstructed from emission data for lines of response and from attenuation coefficients for some but not all of the lines of response.

The objective function for the reconstruction makes use of the known ACF and a model of the ACF derived from the emission information, such as the prompt data, for the unknown ACF. TOF prompt data y with spatial projection (LOR) index i and TOF bin index t, may be modeled by combining the modeled projection $\bar{p}$ from the emission object f, corrected for scanner efficiency by a normalization array N and for attenuation by the inverse of the attenuation factors (ACFs) A. The background events have a known mean $\bar{b}$, equal to the sum of the estimated efficiency corrected scatter and of the estimated randoms. The Poisson Likelihood objective function has the following form:

$$L(f, A) = \sum_{i,t}\left(y_{it} \ln\left(\frac{\bar{p}_{it}}{N_i A_i} + \bar{b}_{it}\right) - \frac{\bar{p}_{it}}{N_i A_i} - \bar{b}_{it}\right), \quad (1)$$

$$\bar{p}_{i,t} = \sum_{j} C_{it,j} f_j$$

where $C_{ij,t}$ is the system matrix corresponding to the TOF line-integral projector. Quantities without index t denote TOF summed quantities, such as:

$$C_{i,j} = \sum_{t} C_{it,j}, \; y_i = \sum_{t} y_{it}, \; \bar{p}_i = \sum_{t} \bar{p}_{it}, \; \bar{b}_i = \sum_{t} \bar{b}_{it}. \quad (2)$$

The objective function of equation (1) may be optimized with respect to A, assuming fixed $\bar{p}$. Unfortunately, there is no closed form solution in the presence of background events.

The unknown ACF are modeled along the lines of response for which ACF is not known from the CT scan, accounting of the partially known attenuation in act 64. Substitute attenuation coefficients are found for the lines of response without attenuation coefficients. The time of flight data itself includes attenuation information, so may be used to create the model for the missing ACFs. In one embodiment, the model is a Gaussian smoothed function of the time of flight data for the lines of response with missing attenuation information. Other smoothing than Gaussian or no smoothing may be used. A mean of the background events may be included in the model. During iterative reconstruction, the activity image or distribution of a previous iteration of the reconstruction is used to model the ACF for lines of response with missing ACF. The emission data is projected along the lines of response with missing ACF. The model may use normalized, smoothed prompt data, which is pre-corrected for background. Additional, different, or fewer variables or functions may be used.

In one embodiment, a closed form expression is provided for A. A is considered as a function of $\bar{p}$ in the following way:

$$A_i = \begin{cases} A_{i'}, \text{ known } ACFs \\ \dfrac{\bar{p}_i}{N_i \text{smooth}(y_i - \bar{b}_i)} = \dfrac{\bar{p}_i}{N_i \tilde{y}_i} > 0 \end{cases} \quad (3)$$

where the prompt data y is pre-corrected for background events b, represented as $\tilde{y}_i = y_i - \bar{b}_i$. Prime spatial projection indices denote LORs that are entirely contained within the CT volume and for which the ACFs are obtained by re-projecting the CT attenuation map. In the absence of background ($\bar{b}_i = 0$), the second line of equation (3) is the maximizer of the Poisson Likelihood of equation (1) at fixed activity f. In the presence of background, there is no closed form for the maximizer of equation (1). Instead, the expression in equation (3) is used. The expression is the maximizer of the Gaussian approximation of the Poisson Likelihood, with data variance approximated by $\bar{p}$. This allows for the elimination of the ACFs from the optimization by inserting equation (3) into equation (1). This leads to an objective function, which has only an unknown emission image f:

$$L(f) = \qquad (4)$$

$$L_1(f) + L_2(f) + L_3(f) = \sum_{i',t}\left(y_{i't} \ln\left(\dfrac{\bar{p}_{i't}}{N_{i'}A_{i'}} + \bar{b}_{i't}\right) - \dfrac{\bar{p}_{i't}}{N_{i'}A_{i'}} - \bar{b}_{i't}\right) +$$

$$\sum_{i,t} y_{it} \ln(\tilde{y}_i \bar{p}_{it} + \bar{b}_{it}\bar{p}_i) - \sum_i y_i \ln(\bar{p}_i).$$

In an alternative embodiment, the missing ACF is accounted for by maximizing the true Poisson likelihood by alternatively maximizing equation (1) with respect to the ACFs A and with respect to the activity f.

In one embodiment, using the known ACF and the model of ACF where not known, the reconstruction may be free of reconstructing an attenuation distribution. The ACF for the lines of response are used rather than reconstructing a distribution of attenuation. The reconstruction of the activity distribution is performed without reconstructing an attenuation map. The emission map is the only unknown in the objective function.

The objective function of equation (4) is not concave. A monotonic algorithm to optimize equation (4) is formed by constructing surrogate functions. $f^{(n)}$ denotes the current estimation of the unknown activity function, at iteration number n. A surrogate is a function $\Phi(f,f^{(n)})$ that satisfies the following conditions:

$$L(f) \geq \Phi(f,f^{(n)}), L(f^{(n)}) = \Phi(f^{(n)},f^{(n)}) \qquad (5)$$

The (n+1)th estimate of the activity is defined as the maximizer of the surrogate $\Phi(f,f^{(n)})$, and the properties of equation (5) ensure that this update monotonically increases the objective function, i.e. $L(f^{(n+1)}) \geq L(f^{(n)})$. The goal is to construct a surrogate function that is easily optimized with respect to the activity f. A known separable surrogate function for the first term in equation (4) is used in the derivation of the ML-EM algorithm. A similar surrogate may be used for the monotonic optimization of the second term in equation (4). Both surrogates are derived by exploiting the concavity of the logarithm:

$$\ln\left(\sum_j \alpha_j x_j\right) \geq \sum_j \alpha_j \ln(x_j) \qquad (6)$$

$$\sum_j \alpha_j = 1, \text{ and } \alpha_j \geq 0, x_j > 0, j = 1, \ldots, M$$

where the index j runs over all image voxels (j=1, ..., M), and an additional term j=0 is introduced to handle the background term.

The surrogate for $L_1(f)$ is obtained by applying equation (6) to the term containing the logarithm, with each term (i,t) in the sum, $$\alpha_j = \dfrac{\dfrac{C_{i't,j}}{A_{i'}N_{i'}}f_j^{(n)}}{\dfrac{\bar{p}_{i't}^{(n)}}{A_{i'}N_{i'}} + \bar{b}_{i't}} \quad x_j = \left(\dfrac{\bar{p}_{i't}^{(n)}}{A_{i'}N_{i'}} + \bar{b}_{i't}\right)\dfrac{f_j}{f_j^{(n)}} \quad j = 1, \ldots, M \qquad (7)$$

$$\alpha_0 = \dfrac{\bar{b}_{i't}}{\dfrac{\bar{p}_{i't}^{(n)}}{A_{i'}N_{i'}} + \bar{b}_{i't}} \quad x_0 = \dfrac{\bar{p}_{i't}^{(n)}}{A_{i'}N_{i'}} + \bar{b}_{i't}$$

where $\bar{p}_{it}^{(n)} = \sum_j C_{it,j} f_j^{(n)}$.

This yields the first term of the surrogate, which satisfies equation (5), as shown by:

$$\Phi_1(f, f^{(n)}) = \sum_{i',t} y_{i't} \sum_j \dfrac{\dfrac{C_{i't,j}}{A_{i'}N_{i'}}f_j^{(n)}}{\dfrac{\bar{p}_{i't}^{(n)}}{A_{i'}N_{i'}} + \bar{b}_{i't}} \ln\left(\left(\dfrac{\bar{p}_{i't}^{(n)}}{A_{i'}N_{i'}} + \bar{b}_{i't}\right)\dfrac{f_j}{f_j^{(n)}}\right) + \qquad (8)$$

$$\sum_{i',t} y_{i't} \dfrac{\bar{b}_{i't}}{\dfrac{\bar{p}_{i't}^{(n)}}{A_{i'}N_{i'}} + \bar{b}_{i't}} \ln\left(\dfrac{\bar{p}_{i't}^{(n)}}{A_{i'}N_{i'}} + \bar{b}_{i't}\right) - \sum_{i',t}\left(\dfrac{\bar{p}_{i't}}{N_{i'}A_{i'}} + \bar{b}_{i't}\right)$$

The surrogate for $L_2(f)$ is also obtained by applying equation (6) with, for each term (i,t) in the sum, $$\alpha_j = \dfrac{\tilde{y}_i C_{it,j} f_j^{(n)}}{\tilde{y}_i \bar{p}_{it}^{(n)} + \bar{b}_{it}\bar{p}_i^{(n)}} + \dfrac{\bar{b}_{it} C_{i,j} f_j^{(n)}}{\tilde{y}_i \bar{p}_{it}^{(n)} + \bar{b}_{it}\bar{p}_i^{(n)}} \qquad (9)$$

$$x_j = (\tilde{y}_i \bar{p}_{it}^{(n)} + \bar{b}_{it}\bar{p}_i^{(n)})\dfrac{f_j}{f_j^{(n)}} \quad j = 1, \ldots, M$$

This yields the second term of the surrogate, which satisfies equation (5) as shown by:

$$\Phi_2(f, f^{(n)}) = \sum_{i,t} y_{it} \sum_j \dfrac{(\tilde{y}_i C_{it,j} + \bar{b}_{it} C_{i,j}) f_j^{(n)}}{\tilde{y}_i \bar{p}_{it}^{(n)} + \bar{b}_{it}\bar{p}_i^{(n)}} \ln\left((\tilde{y}_i \bar{p}_{it}^{(n)} + \bar{b}_{it}\bar{p}_i^{(n)})\dfrac{f_j}{f_j^{(n)}}\right) \qquad (10)$$

where $\bar{p}_i^{(n)} = \sum_j \sum_t C_{it,j} f_j^{(n)} = \sum_j C_{i,j} f_j^{(n)}$.

Finally the surrogate for $L_3(f)$ is obtained using the inequality:

$$\ln(x) \leq x - 1 \qquad (11)$$

as follows:

$$L_3(f) \equiv -\sum_i y_i \ln\left(\frac{p_i}{\bar{p}_i^{(n)}}\right) - \sum_i y_i \ln(\bar{p}_i^{(n)}) \geq \Phi_3(f, f^{(n)}) = \quad (12)$$

$$-\sum_i y_i \left(\frac{p_i}{\bar{p}_i^{(n)}} - 1\right) - \sum_i y_i \ln(\bar{p}_i^{(n)})$$

The (n+1)th estimate of the activity is defined as the maximizer of the surrogate, and is obtained by solving $0=\nabla_f(\Phi_1(f, f^{(n)})+\Phi_2(f,f^{(n)})+\Phi_3(f,f^{(n)}))$ for f. Since the surrogate is separable, this equation is solved separately for each voxel k as $$0 = \frac{\partial}{\partial f_k}(\Phi_1(f, f^{(n)}) + \Phi_2(f, f^{(n)}) + \Phi_3(f, f^{(n)})) = \quad (13)$$

$$\sum_{i',t} y_{i't} \frac{\frac{C_{i't,k}}{A_{i'}N_{i'}}}{\frac{\bar{p}_{i't}^{(n)}}{A_{i'}N_{i'}} + \bar{b}_{i't}} \frac{f_k^{(n)}}{f_k} - \sum_{i',t} \frac{C_{i't,k}}{A_{i'}N_{i'}} +$$

$$\sum_{i,t} y_{it} \frac{\tilde{y}_i C_{it,k} + \bar{b}_{it} C_{i,k}}{\tilde{y}_i \bar{p}_{it}^{(n)} + \bar{b}_{it} \bar{p}_i^{(n)}} \frac{f_k^{(n)}}{f_k} - \sum_i y_i \frac{C_{i,k}}{p_i^{(n)}}$$

The solution yields the monotonic objective function for the maximization of equation (4):

$$f_j^{(n+1)} = \frac{f_j^{(n)}}{\sum_{i',t} \frac{C_{i't,j}}{N_{i'}A_{j'}} + \sum_i C_{i,j}\frac{y_i}{p_i^{(n)}}} \quad (14)$$

$$\left\{\sum_{i',t} C_{i't,j} \frac{y_{i't}}{\bar{p}_{i't}^{(n)} + N_{i'}A_{j'}\bar{b}_{i't}} + \sum_{i,t} \frac{y_{it}}{\tilde{y}_i \bar{p}_{it}^{(n)} + \bar{b}_{it}\bar{p}_{it}^{(n)}}(C_{it,j}\tilde{y}_i + C_{i,j}\bar{b}_{it})\right\}$$

Recall that non-TOF projector and backprojector with system matrix $$C_{i,j} = \sum_t C_{it,j}$$

are used in addition to the TOF.

Equation (14) is an objective function for reconstructing the activity distribution. Where the ACF is known (represented by A in equation (14)), the ACF is used. For other locations, the model of the second line of equation (3) is used. For reconstruction, the likelihood of the objective function is maximized iteratively. Other objective functions using a model for ACF from emission data for the unknown ACF may be used.

In act 66, an image is displayed. The reconstructed activity or emission distribution is used to create a PET image. An image is reconstructed by reconstructing the object space and then rendering or imaging from the reconstructed object. The image is of the patient, such as a PET image showing function or uptake of the radiopharmaceutical. The image benefits from modeling of the ACF using the emission data for some lines of response by having greater sensitivity at the edges of the field of view despite the unknown ACFs for some LORs.

This reconstruction may be simulated to show the desired effects. For example, data corresponding to the geometry of a Siemens mCT scanner is simulated using emission activity and attenuation maps derived from patient data. The images have 400×400×109 (2×2×2 mm) voxels. The activity image is uniform except for a few spheres inserted into various planes. The spheres have 15 and 10 mm diameters and various sphere-to-background ratios. Other arrangements or simulations may be used.

To simulate an attenuated trues sinogram, the activity and attenuation map images are forward projected according to the mCT geometry. A uniform sinogram background with total counts of 30% of total trues is added to simulate a prompt sinogram. Poisson noise is added to the prompt sinogram. Two data sets are simulated with 30 true Mcounts (low count case) and 300 true Mcounts (high count case). Other arrangements may be used.

Two cases are considered first to show the reduction in sensitivity caused by the unknown ACF. In the first case, the attenuation map is assumed as known for the whole volume (109 slices). In the second case, the attenuation map is known only from plane 0 to plane 54, and the activity in that limited axial field of view covered by the known attenuation map is of interest for reconstruction. The ACFs of LORs crossing the attenuation map volume beyond plane 54 are then treated as unknown. Note that this is done without taking into account the support of the image. A more modest truncation of the set of known ACFs is possible, however, if the image support is known to be smaller than the whole transverse field of view.

Figure 7B:
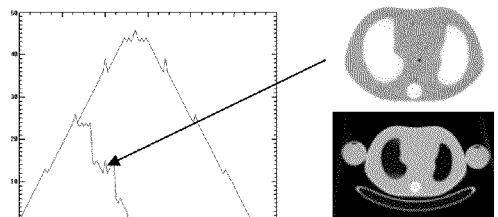
FIGS. 7A and 7B are example sensitivity profiles of simulations.
Figure 7A:
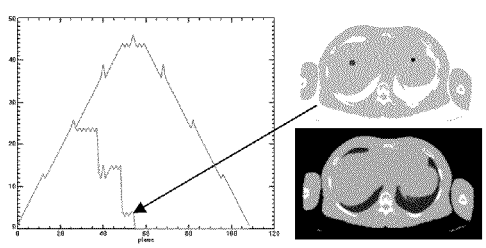

The sensitivity profiles for the two cases are presented in FIG. 7A, where the arrow indicates the central activity image plane (plane 54) containing the centers of two spheres of 15 and 10 mm diameters. This plane corresponds to the lowest sensitivity in truncated ACFs case. For the quantitative analysis, the sphere-to-background ratio is computed over the part of the spheres contained within the known attenuation region, i.e. from planes 0 to 54 (slightly more than half the spheres included in that region). The cylindrical background region is extended over 7 edge planes (planes 48 to 54).

From equation (3), the unknown ACFs cannot be estimated for LORs that are not passing through the support of the activity image (i.e. LORs with $\bar{p}_i$>0). These LORs are assumed to have ACFs equal to 1, are treated as LORs with known ACFs equal to 1, and are therefore attributed a prime index P in equation (14). In other words, the known patient boundary mask is imposed in the sinogram when estimating the ACFs.

The reconstruction using the objective function of equation (14) may be tested on actual data. The algorithm is tested on data acquired in list mode format on a Siemens Biograph mCT scanner. An anthropomorphic torso phantom has a water filled cavity to simulate the liver, two air and Styrofoam filled lung-shaped cavities, and a cylindrical spine-like insert. Two cylindrical water-filled containers are placed at the side of the phantom to represent the attenuation due to the arms of a patient. These containers are not radioactive. Other arrangements may be used.

Three hours of acquisition are used to verify the image quality in a high count scan, but other timing may be used. The initial total activity of F-18 is about 3.7 mCi. A high count scan contains about $3.5 \times 10^9$ true coincidence events. The second acquisition, corresponding to the first three minutes of list mode file data, is investigated to assess the noise properties. This second scan contains about $96 \times 10^6$ true coincidence events with an estimated scatter fraction of about 36%. The three minute scan also contains $46 \times 10^6$ random coincidences.

The mCT projection data included 400(radial)×168(azimuthal)×621(axial)×13(TOF) bins. The scatter is estimated assuming knowledge of the full attenuation map and is used below. The randoms are smoothed.

To simulate a partially known attenuation map, the ACFs of LORs crossing the attenuation map volume beyond plane 50 are treated as unknown. For the analysis, the focus is on plane 44, which contains the centers of three spheres of internal diameters 8, 7, and 6 mm. The quantitative analysis uses the sphere of 8 mm diameter using approximately the known sphere ROI. As shown by the sensitivity profile in FIG. 7B, plane 44 (see arrow) has a reduced sensitivity in the case of a partially known attenuation map, although the edge planes have an even lower sensitivity. FIG. 7B shows ISSRB sensitivity profiles of the experimental data. The LORs crossing the FOV beyond plane 50 are excluded in the sensitivity plot with the lesser horizontal extent. The regular (all LORs are included) sensitivity is represented by the curve with the greater horizontal extent.

Contrary to the computer simulated data, the support of the attenuation map is larger than the support of the activity image. Consequently, the estimation of the ACFs of LORs that do not cross the activity image is extremely noisy and unreliable. These ACFs, however, are not used when reconstructing the activity and hence do not influence the final reconstruction.

Three instances of reconstructed data are considered. The gold standard is a regular OS-EM reconstruction with ACFs known across the whole FOV, using all LORs. Another OS-EM reconstruction, corresponding to a reduced sensitivity activity image, uses only LORs of known ACFs. For example, only direct plane LORs are used to reconstruct the edge planes. The third reconstruction is performed by the objective function of equation (14) and uses the known ACF LORs along with emission-based estimates for the unknown ACF LORs. The initial condition is the same for all algorithms. The initial condition is uniform, with a value close to the background value of the expected image. Since the initial condition support is larger than the true image, the initial projection is always higher in value when compared to the expected projection value from the image. This results in a higher value activity image at early iterations in the region where the scaling parameter is difficult to recover.

The ACF estimate in equation (3) is applied to unsmoothed and smoothed measured data corrected for background events. The smoothing is done with boxcar filtering by a 5×5×5 sinogram bin mask. Reconstruction with pre-smoothed measured data in equation (3) is referred to as smoothed ACFs reconstruction.

Figure 9:
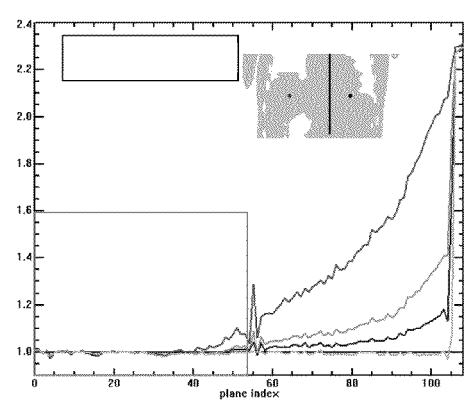
FIG. 9 represents example coronal profile and views for reconstruction from noise-free data.

FIG. 9 presents reconstructions from noise-free data. The profiles are stacked from top to bottom as 4 iterations, 10 iterations, 15 iterations, 50 iterations, and true. The box covering 0-1.6 and 0-54 highlights the part of the emission image where the attenuation map is known. Only this part of the emission image needs to be reconstructed. Nevertheless, due to the connection of the rest of the emission volume to this particular part of the image through oblique LORs, the entire emission volume may be reconstructed. At early iterations, a fine line in the activity background is visible. This line separates the activity region of the known attenuation map from the rest. This line is also reflected in the profile plots as a spike of activity in the border plane 55. This line may help to read the image and separate the attenuation map FOV from the rest of the image.

The top part of the images (left part in the profiles) converge similar to regular OS-EM reconstruction. The ACFs are mostly known and quantitatively the image is correct, even at the first iteration. Contrary to this, the bottom part of the images (the right part in the profile beyond plane 54) is slow in recovering the true activity value. This part of the image is reconstructed without knowledge of the ACFs. The value depends on the initial condition at the early iterations. Nevertheless, the estimated ACFs and corresponding activity image regions slowly converged to correct values even in this region. This is possible due to the interconnection of direct LORs with known attenuation and oblique LORs of unknown attenuation through reconstructed images. A relatively high iteration number, 50, completely removes the influence of the initial condition. Nevertheless, a few bottom edge slices of the image may not converge to the correct value due to the finite image support when oblique LORs do not contribute to edge slices. Therefore, this part of the image is reconstructed from direct plane LORs only and has no connection to the rest of the image volume. Its value depends on the initial condition.

The right edge planes in the volume of interest (plane 54) converge relatively quickly to the correct value in about 10 iterations. This area is dominated by contributions from the oblique LORs with unknown ACFs, and only direct plane LORs posses knowledge of the ACFs. FIG. 9 also shows views of the emissions at plane 54 for different iterations.

The following concentrates on bias in 7 edge planes in the volume of interest since this part of the image shows the performance of the objective function of equation (14) with respect to the correct definition of the ACF scaling parameter.

Figure 10:
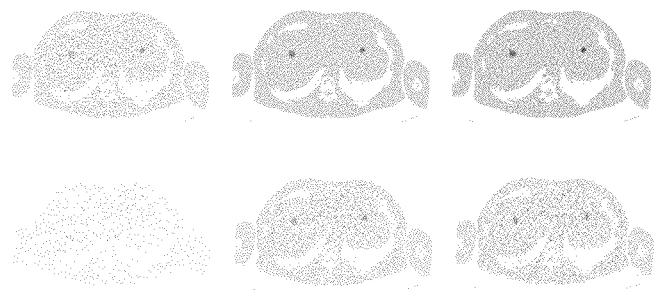
FIG. 10 shows simulated reconstructions.

FIG. 10 represents reconstruction from noise data. In FIG. 10, computer simulation reconstructions at 10 iterations, 24 subsets, for different reconstruction approaches are shown. Reconstruction of slice 54 by (a,d) OS-EM algorithm with only LORs of known ACFs; (b,e) OS-EM algorithm with known across the whole FOV; and (c,f) using known ACF with an emission data model for unknown ACF method. Reconstructions from high count data are presented in (a)-(c); reconstructions from low count data are presented in (d)-(f). The approach of the objective function of equation (14) restores edge slice image sensitivity. Noise texture is similar to the gold standard.

Figure 11:
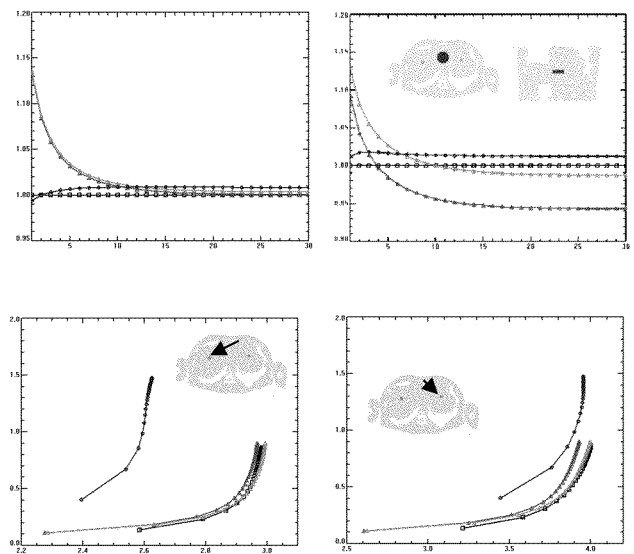
FIG. 11 shows example quantitative assessment of simulated reconstructions.

FIG. 11 shows computer simulation reconstruction quantitative assessment. (a) and (b) show change in background value versus iteration number. The horizontal line corresponds to using all known ACFs, and the upward curving more horizontal line corresponds to using partially known ACFs for a reduced sensitivity image. The two downward curving lines correspond to estimated smooth and estimated unsmoothed ACFs using equation (14). The background value is normalized by a gold standard image and is computed in cylindrical ROI over 7 edge planes (48-54). Plot (a) corresponds to reconstruction from high count data. Plot (b) corresponds to reconstruction from low count data. (c) and (d) show background noise versus sphere to background ratio in reconstruction from high count data. Each point on the curve corresponds to iteration number. Sphere of (c) 15 mm diameter with sphere/background ratio 3:1 and (d) 10 mm diameter and ratio 4:1 is simulated.

FIG. 11 (a) shows that the initial condition bias quickly reduces with iteration number at the edge of the attenuation map FOV (plane 48-54). FIG. 11 (b) shows that bias may be observed in reconstructions from high noise level data if measured data are used as-is. However, the smoothed ACFs method removed this bias. High count data also showed that resolution-bias trade-off of the objective function of equation 14 is very close to gold standard OS-EM reconstruction, according to FIG. 11 (c,d). This trade-off significantly worsened in reduced sensitivity imaging. Observed reduced sphere contrast in one case of reduced sensitivity imaging (FIG. 11 (c)) may be attributed to a significant level of noise, where the contrast definition is not reliable.

Figure 12:
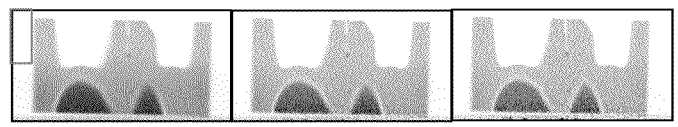
FIGS. 12 and 13 illustrate example convergence of reconstruction.
Figure 13:
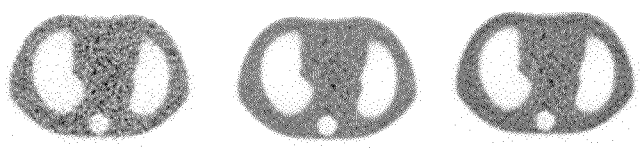

FIG. 12 shows convergence in a case of high count experimental data. A coronal view of reconstruction by (a) 4 iterations; (b) 10 iterations; (c) 15 iterations with 24 subsets is presented. FIG. 13 shows experimental low count data reconstructions of 10 iterations, 24 subsets. Reconstruction of slice 44 by (a) OS-EM algorithm with only LORs of known ACFs; (b) OS-EM algorithm with known across the whole FOV; and (c) using equation (14). Images are post-smoothed by boxcar filtering with a 3×3×3 image voxel mask.

FIGS. 12 and 13 represent reconstruction of a torso phantom. A high count case shows results similar to a computer simulation trend where an activity image tends to recover its true value (not inherited from the initial condition) in a number of iterations. Low count case images of FIG. 13 are post-smoothed and the equation (14) method image resembles the gold standard, although the noise texture seems to be different. The largest 8 mm diameter sphere may be seen in both images. Reduced sensitivity imaging significantly visually reduces sphere detectability, even though the considered slice is not the worst sensitivity plane.

Figure 14:
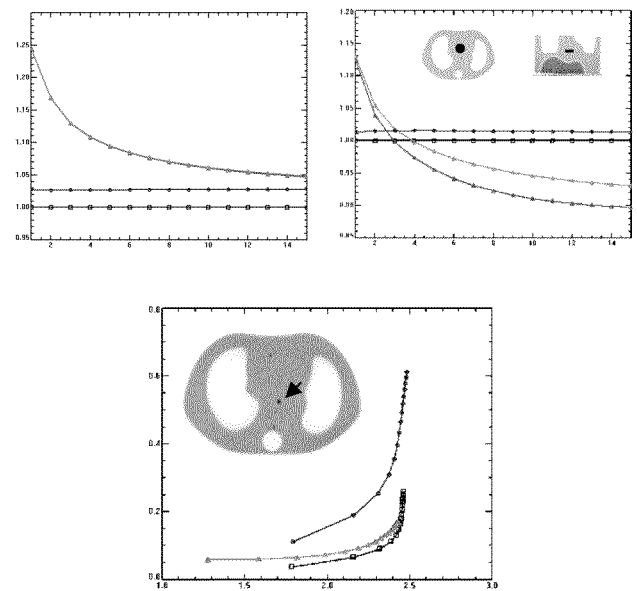
FIG. 14 illustrate change in background value verses iteration number in one example.

FIG. 14 shows experimental data quantitative assessment. FIGS. 14 (a) and (b) show change in background value versus iteration number. The background value is normalized by the gold standard image and is computed in cylindrical ROI over 7 edge planes (44-50). Plot (a) corresponds to reconstruction from high count data. Plot (b) corresponds to reconstruction from low count data. (c) shows background noise versus sphere to background ratio in reconstruction from high count data. The sphere size is 8 mm diameter with 4:1 targeted ratio. One curve represents the gold standard image. Another curve represents a reduced sensitivity image. Two other curves represent an image using equation (14) where no smoothing is used and where smoothing is used in measured data in equation (3).

FIG. 14 (a) shows that initial condition bias quickly reduces with iteration number at the edge of the attenuation map FOV in high count data. Similar to the computer simulations, FIG. 14 (b) shows that in high noise, non-smoothed measured data, bias may be observed. The Smoothed ACFs method reduces this bias but did not remove it completely. High count data shows that resolution-bias trade-off of the equation (14) approach is close to the gold standard reconstruction, according to FIG. 14 (c). As in the case of computer simulations, the equation (14) approach (e.g., using known ACF and an emission-based ACF model of LORs with unknown ACF) shows slightly slower convergence.

Figure 15:
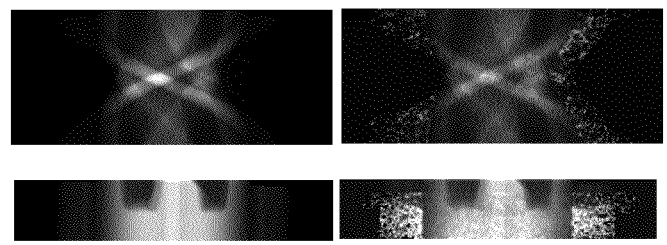
FIG. 15 shows examples of low count data ACF estimation.

FIG. 15 shows experimental low count data ACF estimations at 15 iterations, 24 subsets. Smoothing is used in the constraint of equation (3). (a) is a trans axial view of segment +2 plane. This plane corresponds to sphere plane 44 in SSRB. (a) presents a gold standard CT derived ACF sinogram and (b) presents estimated ACF sinogram. A coronal view of whole segment +2 is presented in (c) and (d): (c) shows CT derived ACF sinogram and (d) shows estimated ACF sinogram. Paired sinograms are scaled to the same maximum value. Estimated ACF sinogram has values lower than 1.

FIG. 15 shows low count data ACFs estimation according to equation (3). ACFs resemble the CT gold standard well, but with slightly reduced ACF in the volume of interest values in the area of highest attenuation at the center of the sinogram. In high count experimental data, the ACFs match CT ACFs quite well even in this region. ACFs may not be reliably defined for LORs passing outside the activity sinogram support. ACFs of cold phantom arms have extremely high values and values below 1. Nevertheless, these ACF values may not influence the final emission image.

The presented reconstruction using known ACF for some LORs and emission-based model of ACF for other LORs shows that ACFs may be estimated directly without attenuation map reconstruction. A drawback of this approach is that ACFs and activity scaling parameters may not be defined. However, the correct value is recovered due to a mix of LORs of known and estimated ACFs through activity image reconstruction. The high count data shows good agreement with the gold standard approach. Additional constraints, such as smoothing of measured data, may not be needed. Low count data reconstruction suggests that smoothing of measured data is beneficial and may justify deviation from the Poisson model in the ACF activity constraint of equation (3). The small bias observed in reconstruction may be attributed to problem nonlinearity, where noise may be converted to bias.

The presented monotonic algorithm may be used without prior attenuation map knowledge, where the prime spatial index set is zero in equation (3). Nevertheless, the algorithm may absorb a known value constraint on any LOR ACFs even between algorithm iterations.

The presented examples show reconstructed images for all FOV, even though only part of the images is of interest. The image may be constructed in shorter volume, when only LORs, passing through CT volume at least partially, are considered in system matrix modeling.

Observed bias in image planes, corresponding to the edge of the attenuation map FOV, is interesting from a theoretical point of view. Such image planes may have a defined scale value due to direct LORs of known ACFs. Therefore, it might be possible to simply rescale the value of these edge planes between iterations.

Using an objective function incorporating known ACF as well as a model of ACF for LORs with unknown ACF may provide more uniform sensitivity PET images. For the situations where object over-scanning occurs, estimation of unknown ACFs may avoid more x-rays. A monotonic algorithm is derived. The complexity of the algorithm and convergence rate is similar to that of the OS-EM algorithm. This makes the reconstruction a suitable replacement for OS-EM in reconstruction with partially known ACFs. The ACFs estimation is a sub-product of the activity estimation in this procedure and is neither used directly nor is an object of interest.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for reconstructing in positron emission tomography with partially known attenuation, the method comprising:

acquiring, with a computed tomography (CT) scanner, attenuation information for a CT volume of a patient;

acquiring, with a positron emission tomography (PET) scanner having a plurality of detectors, time of flight data along lines-of-response from emissions;

converting the attenuation information into attenuation coefficients along only a first subset of a plurality of the lines of response, a second sub-set of the lines of response missing attenuation information;

reconstructing an image of the patient from the time of flight data including the lines of response of the first and second subsets, the reconstructing being a function of the attenuation coefficients along the lines of response of the first subset and a model of attenuation coefficients along the lines of response of the second subset, the model being a function of the corresponding time of flight data for the lines of response of the second sub-set; and displaying the image.

2. The method of claim 1 wherein acquiring the attenuation information comprises acquiring CT data representing voxels of the CT volume.

3. The method of claim 1 wherein acquiring the time of flight data comprises obtaining the time of flight data from different discrete, overlapping bed positions.

4. The method of claim 1 wherein acquiring the time of flight data comprises obtaining the time of flight data during continuous bed motion.

5. The method of claim 1 wherein acquiring the time of flight data comprises acquiring the time of flight data for oblique ones of the lines of response, the lines of response of the second sub-set being oblique lines of response extending beyond the CT volume.

6. The method of claim 1 wherein converting comprises converting for the lines of response with the attenuation information for all locations through a patient along the lines of response and not converting for the lines of response with at least a portion of the line of response missing attenuation information of the patient.

7. The method of claim 1 wherein reconstructing comprises reconstructing without reconstructing an attenuation map.

8. The method of claim 1 wherein reconstructing comprises reconstructing with the model comprising a Gaussian smoothed function of the time of flight data of the second sub-set.

9. The method of claim 8 wherein reconstructing comprise reconstructing the model as a function of the time of flight data and a mean of background events.

10. The method of claim 1 wherein reconstructing comprises reconstructing iteratively, the model being from an activity image of a previous iteration of the reconstructing.

11. The method of claim 1 wherein reconstructing comprises reconstructing with an objective function having an emission map as an only unknown and having the attenuation coefficients of the lines of response of the first subset and not of the lines of response of the second subset.

12. The method of claim 11 wherein reconstructing comprises maximizing a likelihood of the objective function, the objective function comprising:

$$f_j^{(n+1)} = \frac{f_j^{(n)}}{\sum_{i',t} \frac{C_{i't,j}}{N_{i'} A_{j'}} + \sum_i C_{i,j} \frac{y_i}{\overline{p}_i^{(n)}}}$$

$$\left\{ \sum_{i',t} C_{i't,j} \frac{y_{i't}}{\overline{p}_{i't}^{(n)} + N_{i'} A_{j'} \overline{b}_{i't}} + \sum_{i,t} \frac{y_{it}}{\tilde{y}_i \overline{p}_{it}^{(n)} + \overline{b}_{it} \overline{p}_i^{(n)}} (C_{it,j} \tilde{y}_i + C_{i,j} \overline{b}_{it}) \right\}$$

Where f is the emission map, C is a system matrix, b is background, p is a modeled projection, y is prompt data of the time of flight data, and y~ is the prompt data pre-corrected for background events, n is an iteration number, j is an index over all image voxels, i is a line of response index, and t is a time of flight bin index.

13. The method of claim 1 wherein displaying the image comprises displaying a PET image.

14. A non-transitory computer readable storage medium having stored therein data representing instructions executable by a programmed processor for reconstructing in positron emission tomography (PET) with partially known attenuation, the storage medium comprising instructions for:

reconstructing a PET emission distribution from emission data for lines of response and from attenuation coefficients for some but not all of the lines of response, the reconstructing being free of reconstructing an attenuation distribution; and generating a PET image from the PET emission distribution.

15. The non-transitory computer readable storage medium of claim 14 further comprising acquiring the attenuation coefficients for only for a subset of oblique ones of the lines of response, the lines of response without the attenuation coefficients being for other oblique ones of the lines of response passing outside of a computed tomography volume.

16. The non-transitory computer readable storage medium of claim 15 wherein the other oblique ones of the lines of response are from beginning and ends of continuous bed motion.

17. The non-transitory computer readable storage medium of claim 14 wherein reconstructing comprises reconstructing with substitute attenuation coefficients for the lines of response without attenuation coefficients, the substitute attenuation coefficients being a function of a modeled projection of the emission data in the reconstructing and a function of normalized, smoothed prompt data of the emission data, the prompt data pre-corrected for background.

18. The non-transitory computer readable storage medium of claim 14 wherein reconstructing comprises maximization of an objective function, the objective function comprising:

$$f_j^{(n+1)} = \frac{f_j^{(n)}}{\sum_{i',t} \frac{C_{i't,j}}{N_{i'} A_{j'}} + \sum_i C_{i,j} \frac{y_i}{\overline{p}_i^{(n)}}}$$

$$\left\{ \sum_{i',t} C_{i't,j} \frac{y_{i't}}{\overline{p}_{i't}^{(n)} + N_{i'} A_{j'} \overline{b}_{i't}} + \sum_{i,t} \frac{y_{it}}{\tilde{y}_i \overline{p}_{it}^{(n)} + \overline{b}_{it} \overline{p}_i^{(n)}} (C_{it,j} \tilde{y}_i + C_{i,j} \overline{b}_{it}) \right\}$$

where f is the PET emission distribution, C is a system matrix, b is background, p is a modeled projection, y is prompt data of the emission data, and y~ is the prompt data pre-corrected for background, n is an iteration number, j is an index over all image voxels, i is a line of response index, and t is a time of flight bin index.

19. A system for reconstructing in positron emission tomography (PET) with partially known attenuation, the system comprising:

an x-ray scanner configured to obtain attenuation data for a patient volume;

a bed configured to move to scan different parts of a patient in a positron emission tomography (PET) scan;

rings of detectors spaced axially operable to perform the PET scan along lines of response between the detectors, a first set of lines of response oblique to the axial spacing of the detectors extending out of the patient volume; and a processor connected to the detectors, the processor configured to reconstruct activity distribution using time of flight for detected emissions along the lines of response including the first set and others, the activity distribution reconstructed with attenuation corrections from the attenuation data for the others of the lines of response and from the time of flight for the detected emissions for the first set of lines of response.

20. The system of claim 19 wherein the processor is configured to reconstruct the activity distribution without reconstructing a distribution of attenuation.

* * * * *